United States Patent
Zhou

(10) Patent No.: US 12,331,021 B2
(45) Date of Patent: Jun. 17, 2025

(54) TOTAL SYNTHESIS OF PIRFENIDONE

(71) Applicant: Suzhou Fude Zhaofeng Biochemical Technology Co., Ltd, Suzhou (CN)

(72) Inventor: Lihua Zhou, Suzhou (CN)

(73) Assignee: SUZHOU FUDE ZHAOFENG BIOCHEMICAL TECHNOLOGY CO., LTD, Suzhou (CN)

( * ) Notice: Subject to any disclaimer, the term of this patent is extended or adjusted under 35 U.S.C. 154(b) by 962 days.

(21) Appl. No.: 17/434,820

(22) PCT Filed: Sep. 10, 2020

(86) PCT No.: PCT/CN2020/114479
§ 371 (c)(1),
(2) Date: Aug. 30, 2021

(87) PCT Pub. No.: WO2022/051984
PCT Pub. Date: Mar. 17, 2022

(65) Prior Publication Data
US 2022/0251042 A1    Aug. 11, 2022

(51) Int. Cl.
*C07D 213/64*    (2006.01)

(52) U.S. Cl.
CPC .................................. *C07D 213/64* (2013.01)

(58) Field of Classification Search
CPC ..................................................... C07D 213/64
See application file for complete search history.

(56) References Cited

FOREIGN PATENT DOCUMENTS

| CN | 1817862 | A | 8/2006 | | |
|---|---|---|---|---|---|
| CN | 101891676 | A | 11/2010 | | |
| DE | 2362958 | A1 | 6/1974 | | |
| IN | IN2015MU04703 | A | * | 11/2017 | |
| WO | 2003/014087 | A1 | 2/2003 | | |
| WO | WO-2017072216 | A1 | * | 5/2017 | ........... C07D 213/64 |

* cited by examiner

*Primary Examiner* — Joseph K McKane
*Assistant Examiner* — Jalisa Holmes Ferguson
(74) *Attorney, Agent, or Firm* — HAUPTMAN HAM, LLP

(57) ABSTRACT

The present invention relates to a process for the synthesis of Pirfenidone (1) from 5-Methyl-3,4-dihydro-2-pyridone and halobenzene (chlorobenzene, bromobenzene, or iodobenzene) in the presence of a catalytic system consisting of a copper salt and an organic ligand, in the presence of a base.

8 Claims, No Drawings

TOTAL SYNTHESIS OF PIRFENIDONE

RELATED APPLICATIONS

The present application is a U.S. National Phase of International Application Number PCT/CN2020/114479 filed Sep. 10, 2020.

FIELD OF THE INVENTION

The present invention relates to a process for the synthesis of Pirfenidone (1) from 5-Methyl-3,4-dihydro-2-pyridone and halobenzene (chlorobenzene, bromobenzene, or iodobenzene) in the presence of a catalytic system consisting of a copper salt and an organic ligand, in the presence of a base. Compared to 5-methylpyridin-2 (1H)-one, 5-Methyl-3,4-dihydro-2-pyridone is more readily available and less expensive. Also the process exploits the high efficiency of the catalytic system consisting of Copper(I) salt and an organic ligand in the coupling of 5-Methyl-3,4-dihydro-2-pyridone and halobenzene. In addition, the copper-catalyzed aerobic oxidation can effectively transform the motif of 3,4-dihydro-2-pyridone to pyridin-2(1H)-one, leading to a practical synthesis of Pirfenidone.

BACKGROUND OF THE INVENTION

Pirfenidone, chemically known as 5-methyl-1-phenylpyridin-2(1H)-one, is represented by formula (1).

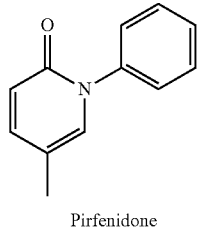

Pirfenidone (1)

Pirfenidone, is a medicament for the treatment of idiopathic pulmonary fibrosis. It has antifibrotic and anti-inflammatory activities, preventing collagen production and fibroblast proliferation.

The synthesis of Pirfenidone has been described in several literatures, and numerous examples rely on 5-methylpyridin-2-amine (2) to make 5-methylpyridin-2(1H)-one (3) which could be transformed to Pirfenidone by arylation.

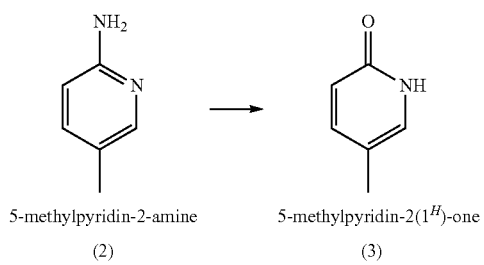

5-methylpyridin-2-amine
(2)

5-methylpyridin-2(1$^H$)-one
(3)

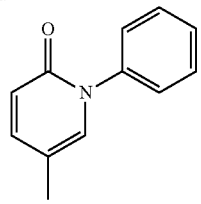

5-methyl-1-phenylpyridin-2(1$^H$)-one

Pirfenidone (1)

Patent DE2362958 discloses the arylation step in the synthesis of Pirfenidone from intermediate (3) by using iodobenzene, copper powder and an inorganic base in the absence of solvent under refluxing temperature.

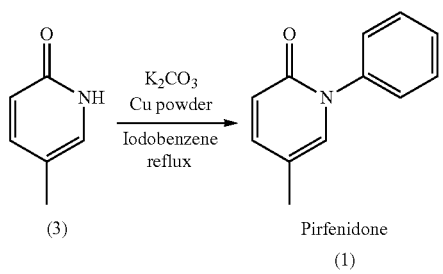

Patent CN1817862 discloses the neat reaction of (3) and iodobenzene promoted by CuCl in the presence of potassium carbonate under refluxing temperature.

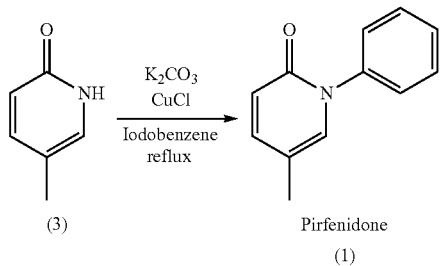

WO2003014087 reports the synthesis of (1) by reacting intermediate (3) with bromobenzene at high temperatures in the presence of potassium carbonate and cuprous oxide.

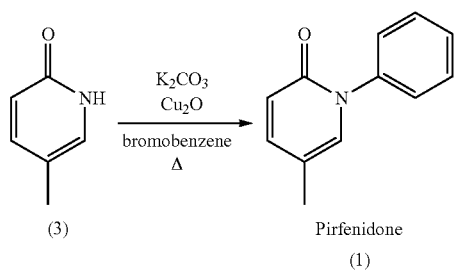

In patent CN101891676 the reaction between (3) and bromobenzene is performed without extra solvent in the presence of CuBr and potassium carbonate under refluxing temperature of bromobenzene.

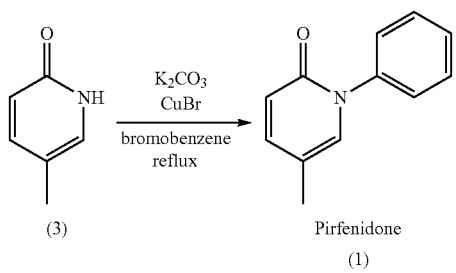

WO2017072216 reports the synthesis of (1) by reacting intermediate (3) with chlorobenzene at high temperatures in the presence of potassium carbonate and a catalytic system consisting of a copper salt and an organic ligand.

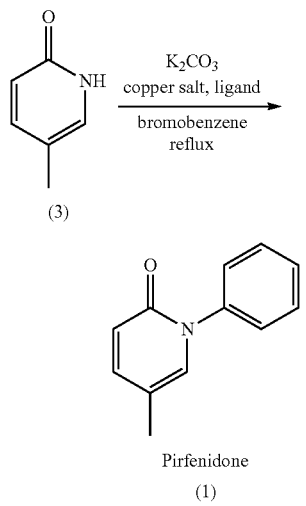

The above mentioned synthetic routes for Pirfenidone all involve the coupling reaction of 5-methylpyridin-2(1H)-one with halobenzene. 5-Methylpyridin-2(1H)-one is usually prepared from 5-methylpyridin-2-amine or 2-methoxy-5-methylpyridine, both of which require transition-metal catalyzed coupling reaction for their synthesis, leading to the higher cost for the total synthesis of Pirfenidone.

Therefore, there still remains a need to improve such process and develop an efficient, simple and industrially viable synthetic route, which can overcome the drawbacks of the prior art.

In order to overcome the problems associated with the prior art, it is herein described a new and improved process which provides Pirfenidone in higher yield using cheaper reagents.

DEFINITIONS

The following definitions are used in connection with the present application, unless it is indicated otherwise.

The term "room temperature" refers to a temperature ranging from about 15° C. to 35° C., preferably to a temperature ranging from about 20° C. to 30° C., more preferably to a temperature of 25° C.

The term "alkyl" refers to a straight or branched chain hydrocarbon containing from 1 to 12 carbon atoms. Representative examples of alkyl include, but are not limited to, methyl, ethyl, n-propyl, iso-propyl, n-butyl, sec-butyl, iso-butyl, tert-butyl, n-pentyl, iso-pentyl, neopentyl, n-hexyl, 3-methylhexyl, 2,2-dimethylpentyl, 2,3-dimethylpentyl, n-heptyl, n-octyl, n-nonyl, and n-decyl.

The term "aryl" refers to a monocyclic-ring system or a polycyclic-ring system wherein one or more of the fused rings are aromatic. Representative examples of aryl include, but are not limited to, anthracenyl, fluorenyl, indanyl, indenyl, naphthyl, and phenyl.

ABBREVIATIONS

| | |
|---|---|
| ppy | 2-phenylpyridine |
| bpy | 2,2'-bipyridine |
| bpz | bipyrazyl |
| dtbbpy | 4,4-di-tert-butyl-2,2'-bipyridine |
| TBHP | tert-butyl hydroperoxide |

SUMMARY OF THE INVENTION

In one aspect, a method for manufacturing Pirfenidone of Formula (1),

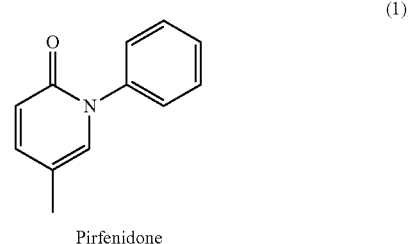

which comprises the steps of:

(a) Reacting 5-Methyl-3,4-dihydro-2-pyridone (4) and halobenzene (5) in the presence of a base, a copper catalyst and a ligand to form 5-methyl-1-phenyl-3,4-dihydropyridin-2(1H)-one (6).

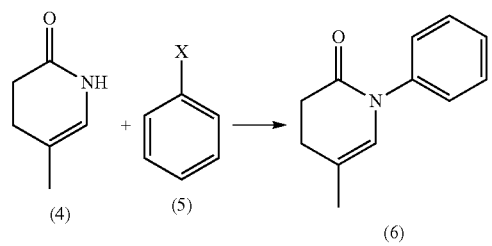

wherein X is selected from the group consisting of —Cl, —Br, and —I.

(b) an oxidation of 5-methyl-1-phenyl-3,4-dihydropyridin-2(1H)-one (6) to Pirfenidone (1) in the presence of a copper catalyst and an oxidant.

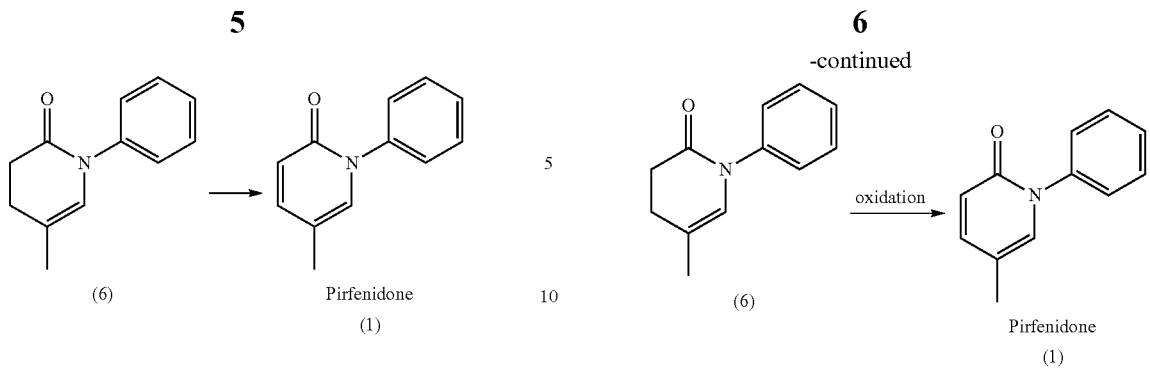

The above process is preferably carried out by isolating intermediate compound, namely 5-methyl-1-phenyl-3,4-dihydropyridin-2(1H)-one. Also preferably, the process is carried out without isolating intermediate 5-methyl-1-phenyl-3,4-dihydropyridin-2(1H)-one. Even more preferably, the above process is carried out as a one-pot reaction, that is, without the need to isolate intermediate 5-methyl-1-phenyl-3,4-dihydropyridin-2(1H)-one, but completing the whole conversion directly to Pirfenidone.

DETAILED DESCRIPTION OF THE INVENTION

The present application is based on the discovery of a novel, alternative approach to synthesizing Pirfenidone. The synthesis described herein allows for the cost-effective preparation of Pirfenidone by using cheap and easily available raw materials, new catalyst system, which reduce production time and cost.

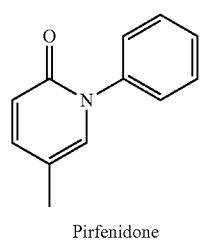

Pirfenidone (1)

This approach provides a step-economical method for the low cost production of pirfenidone. In order to realize a strategy based on cheap, readily available chemical inputs, step economy, and overall efficiency, novel reactions are relied on to build in significant molecular complexity at each synthetic step.

In a first aspect, a synthetic method is provided as outlined below:

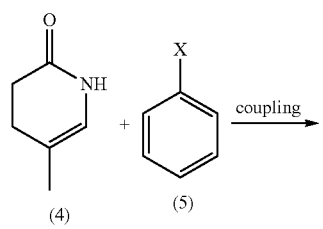

The synthesis is started by the coupling of 5-Methyl-3,4-dihydro-2-pyridone (4) and halobenzene (5) in the presence of a base, a copper catalyst and a ligand to form 5-methyl-1-phenyl-3,4-dihydropyridin-2(1H)-one (6). Halobenzene is selected from chlorobenzene, bromobenzene, and iodobenzene.

The first step is a copper catalyzed C-N coupling. The base herein is selected from any organic and inorganic base such as TEA, DBU, DIPEA, KOH, $K_2CO_3$, NaOH, $Na_2CO_3$, $Cs_2CO_3$, CsOH, $K_3PO_4$, $K_2HPO_4$, $Na_3PO_4$, and $Na_2HPO_4$. Example copper catalysts include CuI, CuCl, CuBr, $Cu_2O$, $Cu(acac)_2$, $CuCl_2$, $CuBr_2$, $CuI_2$, $Cu(OAc)_2$, $Cu(OTf)_2$, $Cu(ClO_4)_2$, and $CuSO_4$. The ligand is selected from compound of formula (7),

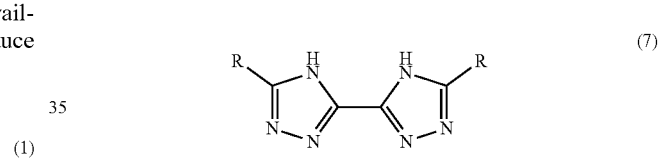

Wherein R is selected from any alkyl and substituted/unsubstituted aryl groups. Preferably, R is selected from methyl, ethyl, propyl, isopropyl, tertbutyl; and substituted/unsubstituted anthracenyl, fluorenyl, indanyl, indenyl, naphthyl, and phenyl groups. Some examples of formula VII are listed as following (L1-L10):

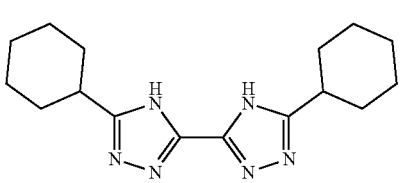

L1

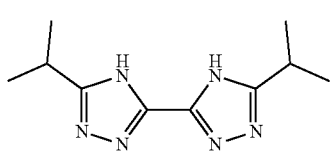

L2

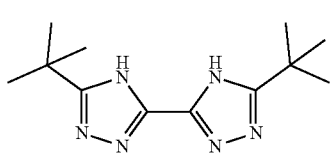

L3

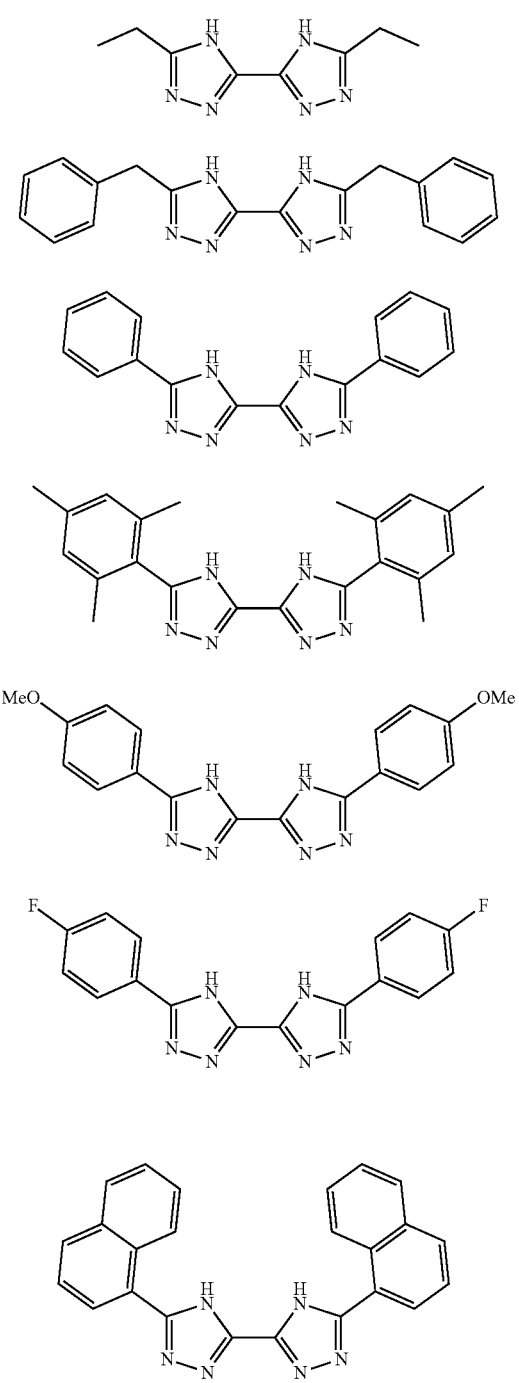

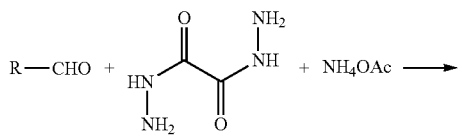

The compound of formula (7) can be prepared by the reaction of an aldehyde, oxalohydrazide and ammonia acetate as showed in following scheme:

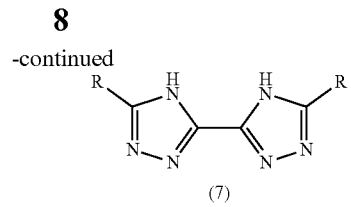

The second step of the synthesis is the oxidation of 5-methyl-1-phenyl-3,4-dihydropyridin-2(1H)-one (6) to Pirfenidone (1) in the presence of a copper catalyst and an oxidizing reagent. The copper catalyst is selected from any copper salts and their complex, such as CuI, CuCl, CuBr, $Cu_2O$, $Cu(acac)_2$ $CuCl_2$, $CuBr_2$, $CuI_2$, $Cu(OAc)_2$, $Cu(OTf)_2$, $Cu(ClO_4)_2$, and $CuSO_4$. The oxidizing reagent is selected from dioxygen, hydrogen peroxide, organic peroxides, inorganic persulfate and inorganic peroxymonosulfate.

Preferably, the total synthesis of Pirfenidone from 5-Methyl-3,4-dihydro-2-pyridone (4) is accomplished in one-pot reaction with the same catalytic system (copper salt and ligand) promoting the two steps in one single reaction vessel:

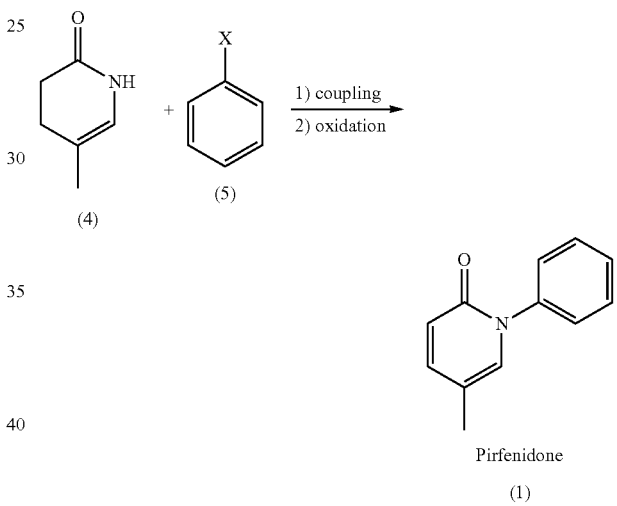

Firstly, to the mixture containing 5-Methyl-3,4-dihydro-2-pyridone (4) and halobenzene (5) is added a base, a copper catalyst and a ligand. After the completion of the coupling reaction of 5-Methyl-3,4-dihydro-2-pyridone (4) and halobenzene (5), to the same reaction vessel is added an oxidizing reagent. The same copper catalyst should promote the oxidation of intermediate (6) to Pirfenidone (1). By this way, there is no need to separate the intermediate (6), and formally one step is saved, meaning less technical operation and chemical input.

Secondly, the compound of formula (7) is firstly employed as the ligand in the coupling reaction of C—N bond. The compound of formula (7) is readily available and it shows high selectivity and efficiency in the coupling reaction. It can be applied to a wide range of substrates with different substituents.

EXAMPLE

As illustrated in following scheme, the example synthesis of Pirfenidone is accomplished in one-pot reaction with the same catalytic system (copper salt and ligand) promoting the two steps in one single reaction vessel:

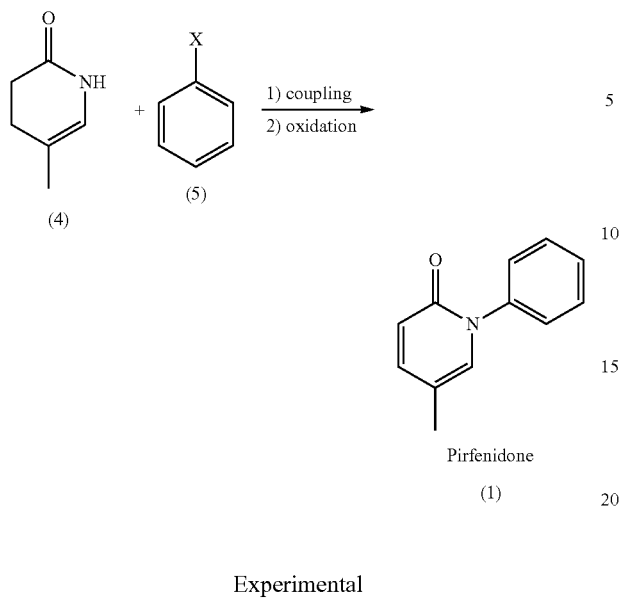

Experimental

Detailed experimental parameters suitable for the preparation of Pirfenidone according to the present invention are provided by the following examples, which are intended to be illustrative and not limiting.

Unless otherwise noted, all materials, solvents and reagents, including anhydrous solvents such as DMF and DMSO, were obtained from commercial suppliers, of the best grade, and used without further purification. All reactions involving air- or moisture-sensitive compounds were performed under nitrogen or argon atmosphere, unless otherwise noted. 5-Methyl-3,4-dihydro-2-pyridone (4) is prepared according to the procedure described in J. Org. Chem. 1991, 56, 2024-2030.

The $^1$H (400 MHz) and $^{13}$C NMR (100 MHz) data were recorded on Bruker AVANCE II 400 MHz spectrometer using CDCl$_3$ or DMSO-D$_6$ as solvent. The chemical shifts (δ) are reported in ppm and coupling constants (J) in Hz. $^1$H NMR spectra was recorded with tetramethylsilane (δ=0.00 ppm) as internal reference; $^{13}$C NMR spectra was recorded with CDCl$_3$ (δ=77.00 ppm) or DMSO-D$_6$ (δ=39.5 ppm) as internal reference.

The synthesis of L1:

To a solution of cyclohexanecarbaldehyde (11.2 g, 100 mmol), oxalohydrazide (6.5 g, 55 mmol), and ammonia acetate (8.5 g, 110 mmol) in methanol (200 mL), was added iodine (2.5 g, 10 mmol). The reaction mixture was refluxed for 20 h before being filtered. The resulted solid was washed with methanol (50 mL) three times and ether (50 mL), then dried under vacuum to afford desired L1 as yellow solid. Yield: 12 g, 80%. $^1$H NMR (400 MHz, CDCl$_3$) δ 11.12; (brs, 2H), 2.69-2.75; (m, 2H), 1.61-1.86; (m, 8H), 1.33-1.63; (m, 12H). $^{13}$C NMR (100 MHz, CDCl$_3$) δ 163.5, 159.3, 39.5, 33.0, 26.1, 26.4. ESI-TOF-HRMS calculated for C$_{16}$H$_{24}$N$_6$Na (M+Na) 323.1960, found 323.1924.

The synthesis of L5:

To a solution of 2-phenylacetaldehyde (12 g, 100 mmol), oxalohydrazide (6.5 g, 55 mmol), and ammonia acetate (8.5 g, 110 mmol) in methanol (200 mL), was added iodine (2.5 g, 10 mmol). The reaction mixture was refluxed for 17 h before being filtered. The resulted solid was washed with methanol (50 mL) three times and ether (50 mL), then dried under vacuum to afford desired L5 as yellow solid. Yield: 12 g, 76%. $^1$H NMR (400 MHz, CDCl$_3$) δ 11.12; (brs, 2H), 7.26-7.30; (m, 4H), 7.18-7.25; (m, 6H), 4.02; (s, 4H). $^{13}$C NMR (100 MHz, CDCl$_3$) δ 163.5, 159.6, 136.5, 129.1, 128.6, 125.5, 34.2. ESI-TOF-HRMS calculated for C$_{18}$H$_{16}$N$_6$Na (M+Na) 339.1329, found 339.1313.

The synthesis of L6:

To a solution of benzaldehyde (10.6 g, 100 mmol), oxalohydrazide (6.5 g, 55 mmol), and ammonia acetate (8.5 g, 110 mmol) in methanol (200 mL), was added iodine (2.5 g, 10 mmol). The reaction mixture was refluxed for 18 h before being filtered. The resulted solid was washed with methanol (50 mL) three times and ether (50 mL), then dried under vacuum to afford desired L6 as yellow solid. Yield: 11 g, 77%. $^1$H NMR (400 MHz, CDCl$_3$) δ 11.12; (brs, 2H), 8.05-8.09; (m, 4H), 7.43-7.51; (m, 6H). $^{13}$C NMR (100 MHz, CDCl$_3$) δ 163.5, 157.6, 132.5, 131.1, 129.2, 127.5. ESI-TOF-HRMS calculated for C$_{16}$H$_{12}$N$_6$Na (M+Na) 311.1021, found 311.1003.

The synthesis of L7:

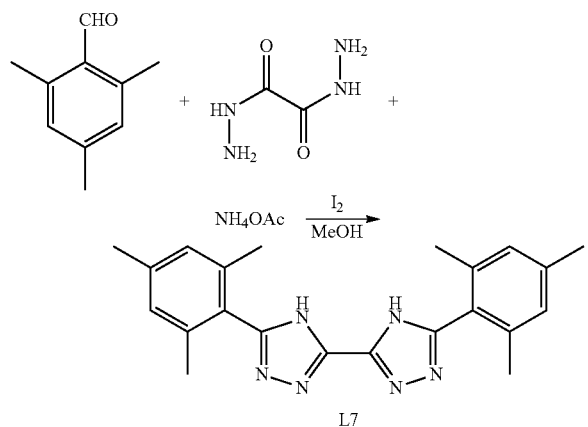

To a solution of 2,4,6-trimethylbenzaldehyde (14.8 g, 100 mmol), oxalohydrazide (6.5 g, 55 mmol), and ammonia acetate (8.5 g, 110 mmol) in methanol (200 mL), was added iodine (2.5 g, 10 mmol). The reaction mixture was refluxed for 24 h before being filtered. The resulted solid was washed with methanol (50 mL) three times and ether (50 mL), then dried under vacuum to afford desired L7 as yellow solid. Yield: 12 g, 65%. $^1$H NMR (400 MHz, CDCl$_3$) δ 11.12; (brs, 2H), 7.01; (s, 4H), 2.57; (s, 12H), 2.48; (s, 6H). $^{13}$C NMR (100 MHz, CDCl$_3$) δ 163.5, 157.6, 138.2, 136.1, 128.2, 122.5, 21.9, 19.3. ESI-TOF-HRMS calculated for C$_{22}$H$_{24}$N$_6$Na (M+Na) 395.1960, found 395.1932.

The synthesis of Pirfenidone with iodobenzene, O$_2$ and L1:

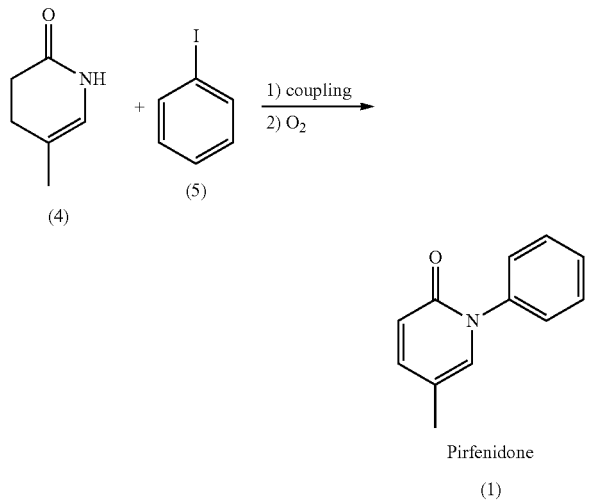

To a solution of 5-methyl-3,4-dihydro-2-pyridone (11.1 g, 100 mmol), iodobenzene (22.4 g, 110 mmol), and K$_3$PO$_4$ (23.3 g, 110 mmol) in DMF (100 mL), was added CuI (1.9 g, 10 mmol) and L1 (3 g, 10 mmol). The reaction mixture was stirred at 100° C. for 10 h before dioxygen was introduced. Then the reaction mixture was stirred at 100° C. for another 8 h with the pressure of O$_2$ maintained at 1 atm. Finally, the reaction mixture was cooled to room temperature and partitioned between ethyl acetate (300 mL) and water (100 mL). The combined organics were dried over MgSO$_4$, filtered and concentrated in vacuum to give a crude product, which was dissolved in ethyl acetate, and hexane is added to the resulting solution; the mixture is left to cool slowly to 5° C. while being stirred, and the resulting pale precipitate is stirred for 1 hour at 5° C. The suspension is filtered under vacuum, and the resulting solid is washed with hexane and dried; crude Pirfenidone (1), with a purity exceeding 95%, is obtained. The beige solid is dissolved in hot water and stirred, in the presence of activated charcoal, for 1 hour. The charcoal is filtered out and washed with hot water. The resulting solution is slowly cooled to room temperature, then stirred at that temperature for 1 hour and cooled to 5° C., stirring for 1 hour. The resulting pale solid is filtered under vacuum, washed with cold water, and dried. Molar yield from 5-methyl-3,4-dihydro-2-pyridone (4) to Pirfenidone (1): 78%.

The synthesis of Pirfenidone with iodobenzene, O$_2$ and L5:

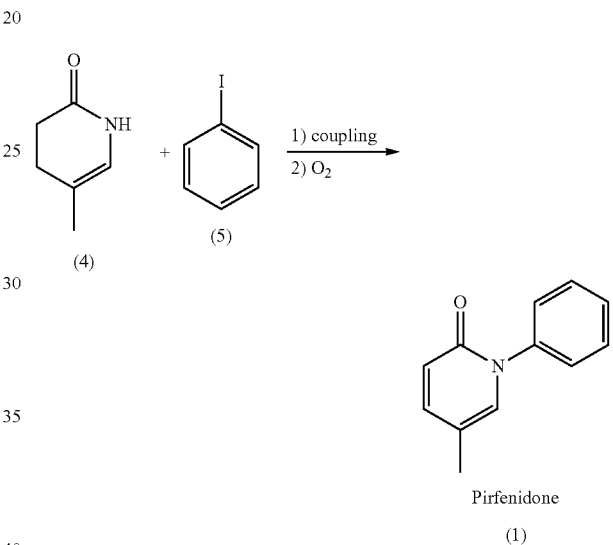

To a solution of 5-methyl-3,4-dihydro-2-pyridone (11.1 g, 100 mmol), iodobenzene (22.4 g, 110 mmol), and K$_3$PO$_4$ (23.3 g, 110 mmol) in DMF (100 mL), was added CuI (1.9 g, 10 mmol) and L5 (3.1 g, 10 mmol). The reaction mixture was stirred at 100° C. for 11 h before dioxygen was introduced. Then the reaction mixture was stirred at 100° C. for another 8 h with the pressure of O$_2$ maintained at 1 atm. Finally, the reaction mixture was cooled to room temperature and partitioned between ethyl acetate (300 mL) and water (100 mL). The combined organics were dried over MgSO$_4$, filtered and concentrated in vacuum to give a crude product, which was dissolved in ethyl acetate, and hexane is added to the resulting solution; the mixture is left to cool slowly to 5° C. while being stirred, and the resulting pale precipitate is stirred for 1 hour at 5° C. The suspension is filtered under vacuum, and the resulting solid is washed with hexane and dried; crude Pirfenidone (1), with a purity exceeding 95%, is obtained. The beige solid is dissolved in hot water and stirred, in the presence of activated charcoal, for 1 hour. The charcoal is filtered out and washed with hot water. The resulting solution is slowly cooled to room temperature, then stirred at that temperature for 1 hour and cooled to 5° C., stirring for 1 hour. The resulting pale solid is filtered under vacuum, washed with cold water, and dried. Molar yield from 5-methyl-3,4-dihydro-2-pyridone (4) to Pirfenidone (1): 75%.

The synthesis of Pirfenidone with bromobenzene, H₂O₂ and L6:

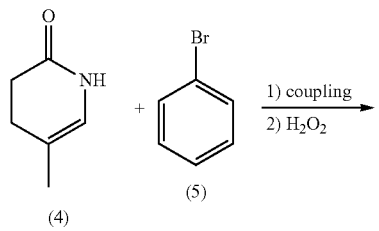

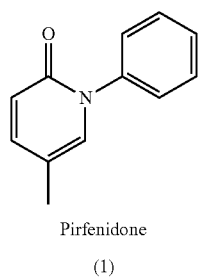

Pirfenidone
(1)

To a solution of 5-methyl-3,4-dihydro-2-pyridone (11.1 g, 100 mmol), bromobenzene (17.2 g, 110 mmol), and K₂CO₃ (15.2 g, 110 mmol) in DMSO (100 mL), was added Cu(OTf)₂ (3.6 g, 10 mmol) and L6 (2.9 g, 10 mmol). The reaction mixture was stirred at 110° C. for 9 h before 20 mL 35% H₂O₂ in water was added. Then the reaction mixture was stirred at 80° C. for another 8 h. Finally, the reaction mixture was cooled to room temperature and partitioned between ethyl acetate (300 mL) and water (100 mL). The combined organics were dried over MgSO₄, filtered and concentrated in vacuum to give a crude product, which was dissolved in ethyl acetate, and hexane is added to the resulting solution; the mixture is left to cool slowly to 5° C. while being stirred, and the resulting pale precipitate is stirred for 1 hour at 5° C. The suspension is filtered under vacuum, and the resulting solid is washed with hexane and dried; crude Pirfenidone (1), with a purity exceeding 95%, is obtained. The beige solid is dissolved in hot water and stirred, in the presence of activated charcoal, for 1 hour. The charcoal is filtered out and washed with hot water. The resulting solution is slowly cooled to room temperature, then stirred at that temperature for 1 hour and cooled to 5° C., stirring for 1 hour. The resulting pale solid is filtered under vacuum, washed with cold water, and dried. Molar yield from 5-methyl-3,4-dihydro-2-pyridone (4) to Pirfenidone (1): 71%.

The synthesis of Pirfenidone with bromobenzene, TBHP and L6:

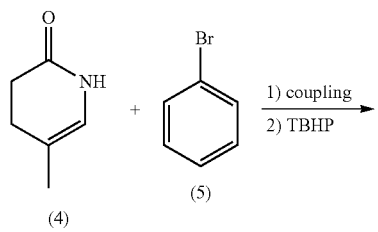

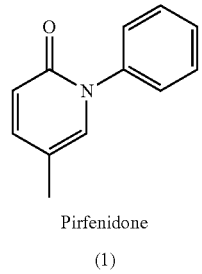

Pirfenidone
(1)

To a solution of 5-methyl-3,4-dihydro-2-pyridone (11.1 g, 100 mmol), bromobenzene (17.2 g, 110 mmol), and Cs₂CO₃ (35.8 g, 110 mmol) in DMSO (100 mL), was added Cu(acac)₂ (2.6 g, 10 mmol) and L6 (2.9 g, 10 mmol). The reaction mixture was stirred at 110° C. for 10 h before TBHP (9.9 g, 110 mmol) was added. Then the reaction mixture was stirred at 80° C. for another 8 h. Finally, the reaction mixture was cooled to room temperature and partitioned between ethyl acetate (300 mL) and water (100 mL). The combined organics were dried over MgSO₄, filtered and concentrated in vacuum to give a crude product, which was dissolved in ethyl acetate, and hexane is added to the resulting solution; the mixture is left to cool slowly to 5° C. while being stirred, and the resulting pale precipitate is stirred for 1 hour at 5° C. The suspension is filtered under vacuum, and the resulting solid is washed with hexane and dried; crude Pirfenidone (1), with a purity exceeding 95%, is obtained. The beige solid is dissolved in hot water and stirred, in the presence of activated charcoal, for 1 hour. The charcoal is filtered out and washed with hot water. The resulting solution is slowly cooled to room temperature, then stirred at that temperature for 1 hour and cooled to 5° C., stirring for 1 hour. The resulting pale solid is filtered under vacuum, washed with cold water, and dried. Molar yield from 5-methyl-3,4-dihydro-2-pyridone (4) to Pirfenidone (1): 72%.

The synthesis of Pirfenidone with chlorobenzene, KHSO₅ and L7:

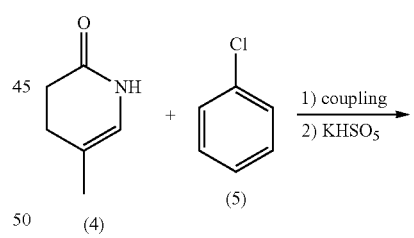

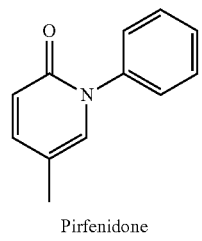

Pirfenidone
(1)

To a solution of 5-methyl-3,4-dihydro-2-pyridone (11.1 g, 100 mmol), chlorobenzene (12.4 g, 110 mmol), and K₂CO₃ (15.2 g, 110 mmol) in CH₃CN (100 mL), was added CuCl (1.0 g, 10 mmol) and L7 (3.7 g, 10 mmol). The reaction mixture was stirred at 100° C. for 10 h before KHSO₅ (16.7 g, 110 mmol) was added. Then the reaction mixture was stirred at 90° C. for another 8 h. Finally, the reaction mixture was cooled to room temperature and partitioned between ethyl acetate (300 mL) and water (100 mL). The combined organics were dried over MgSO4, filtered and concentrated in vacuum to give a crude product, which was dissolved in ethyl acetate, and hexane is added to the resulting solution; the mixture is left to cool slowly to 5° C. while being stirred, and the resulting pale precipitate is stirred for 1 hour at 5° C. The suspension is filtered under vacuum, and the resulting solid is washed with hexane and dried; crude Pirfenidone (1), with a purity exceeding 95%, is obtained. The beige solid is dissolved in hot water and stirred, in the presence of activated charcoal, for 1 hour. The charcoal is filtered out and washed with hot water. The resulting solution is slowly cooled to room temperature, then stirred at that temperature for 1 hour and cooled to 5° C., stirring for 1 hour. The resulting pale solid is filtered under vacuum, washed with cold water, and dried. Molar yield from 5-methyl-3,4-dihydro-2-pyridone (4) to Pirfenidone (1): 70%.

The synthesis of Pirfenidone with chlorobenzene, Na2S2O8 and L7:

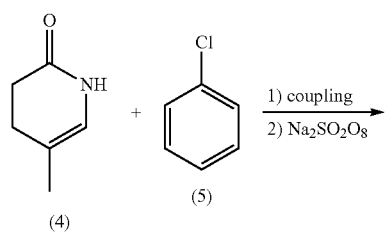

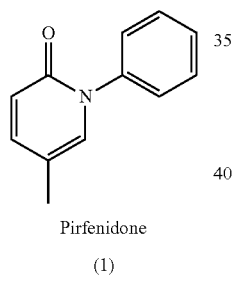

To a solution of 5-methyl-3,4-dihydro-2-pyridone (11.1 g, 100 mmol), chlorobenzene (12.4 g, 110 mmol), and K₂CO₃ (15.2 g, 110 mmol) in DMF (100 mL), was added CuCl (1.0 g, 10 mmol) and L7 (3.7 g, 10 mmol). The reaction mixture was stirred at 100° C. for 9 h before Na₂S₂O₈ (26.2 g, 110 mmol) was added. Then the reaction mixture was stirred at 90° C. for another 7 h. Finally, the reaction mixture was cooled to room temperature and partitioned between ethyl acetate (300 mL) and water (100 mL). The combined organics were dried over MgSO4, filtered and concentrated in vacuum to give a crude product, which was dissolved in ethyl acetate, and hexane is added to the resulting solution; the mixture is left to cool slowly to 5° C. while being stirred, and the resulting pale precipitate is stirred for 1 hour at 5° C. The suspension is filtered under vacuum, and the resulting solid is washed with hexane and dried; crude Pirfenidone (1), with a purity exceeding 95%, is obtained. The beige solid is dissolved in hot water and stirred, in the presence of activated charcoal, for 1 hour. The charcoal is filtered out and washed with hot water. The resulting solution is slowly cooled to room temperature, then stirred at that temperature for 1 hour and cooled to 5° C., stirring for 1 hour. The resulting pale solid is filtered under vacuum, washed with cold water, and dried. Molar yield from 5-methyl-3,4-dihydro-2-pyridone (4) to Pirfenidone (1): 70%.

Pirfenidone (1) obtained from above examples has the following characteristics:
¹H NMR (400 MHz, CDCl₃) δ 7.50-7.44; (m, 2H), 7.43-7.35; (m, 3H), 7.26; (dd, J=2.8 Hz and J=9.3 Hz, 1H), 7.12-7.10; (m, 1H), 6.60; (d, J=9.6 Hz, 1H), 2.10; (s, 3H); ¹³C NMR (100 MHz, CDCl₃) δ 161.6, 142.5, 141.0, 135.2, 129.2, 128.2, 126.5, 121.4, 114.7, 16.9; ESI-TOF-HRMS calculated for $C_{12}H_{12}NO^+$ (M+H+) 186.0913, found 186.0901.

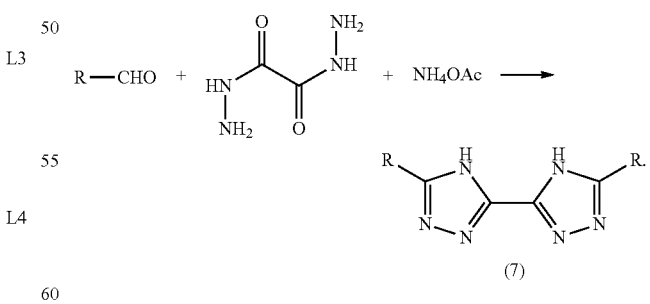

The invention claimed is:
1. A method for manufacturing Pirfenidone of Formula (1),

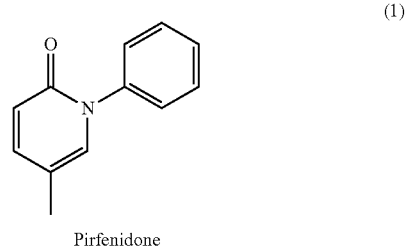

which comprises the steps of:
(a) reacting 5-Methyl-3,4-dihydro-2-pyridone (4) and halobenzene (5) in the presence of a base, a copper catalyst and a ligand to form 5-methyl-1-phenyl-3,4-dihydropyridin-2(1H)-one (6),

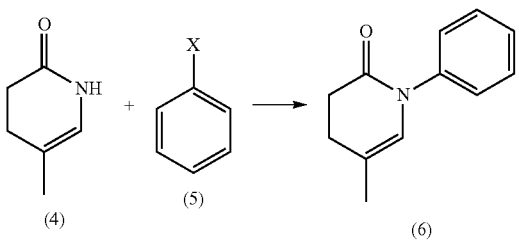

wherein X is selected from the group consisting of —Cl, —Br, and —I,
(b) an oxidation of 5-methyl-1-phenyl-3,4-dihydropyridin-2(1H)-one (6) to Pirfenidone (1) in the presence of a copper catalyst and an oxidant

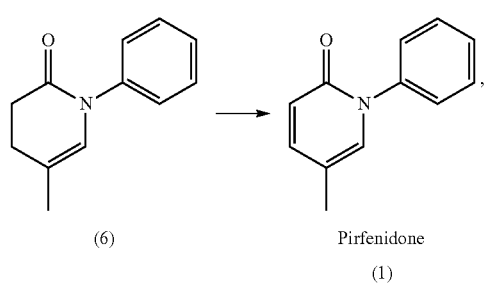

wherein the ligand of step (a) is selected from compound of formula (7), L1 and L5,

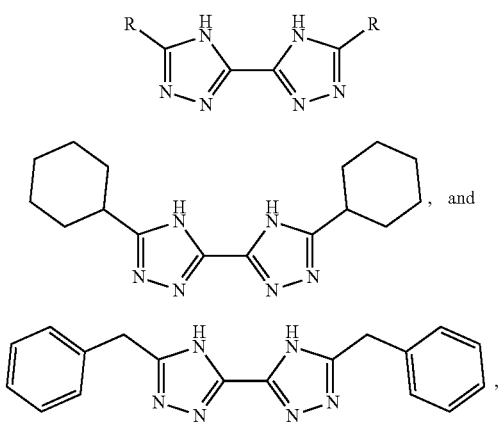

and wherein R is selected from any alkyl and substituted/unsubstituted aryl groups.

2. The method of claim 1, wherein the base of step (a) is selected from TEA, DBU, DIPEA, KOH, $K_2CO_3$, NaOH, $Na_2CO_3$, $Cs_2CO_3$, CsOH, $K_3PO_4$, $K_2HPO_4$, $Na_3PO_4$ and $Na_2HPO_4$.

3. The method of claim 1, wherein the copper catalyst of step (a) and (b) is the same or different, and is selected from CuI, CuCl, CuBr, $Cu_2O$, $Cu(acac)_2$ $CuCl_2$, $CuBr_2$, $CuI_2$, $Cu(OAc)_2$, $Cu(OTf)_2$, $Cu(ClO_4)_2$, and $CuSO_4$.

4. The method of claim 1, wherein the oxidant of step (b) is selected from dioxygen, hydrogen peroxide, organic peroxides, inorganic persulfate and inorganic peroxymonosulfate.

5. The method of claim 1, wherein the R is selected from methyl, ethyl, propyl, isopropyl, tertbutyl; and substituted/unsubstituted anthracenyl, fluorenyl, indanyl, indenyl, naphthyl, and phenyl groups.

6. The method of claim 1, wherein the ligand is selected from the following structures:

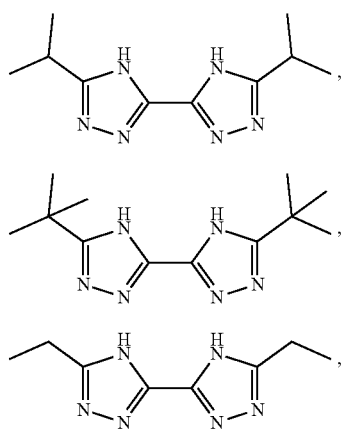

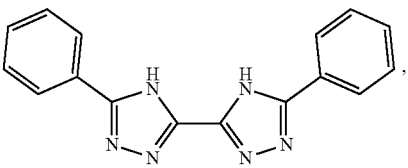

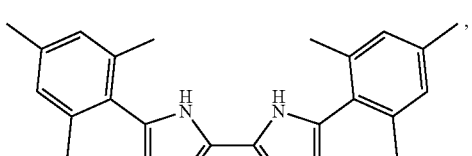

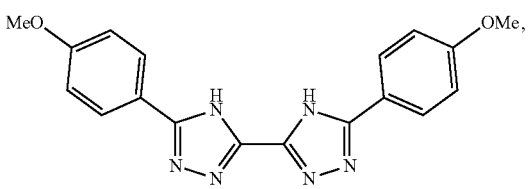

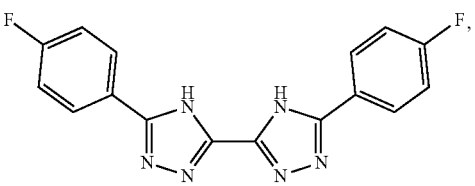

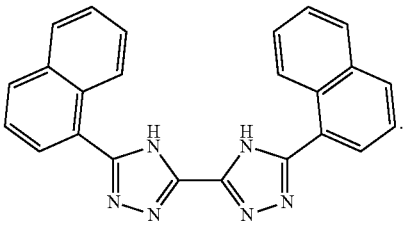

7. The method of claim 1, wherein the step (a) and (b) are carried out as one-pot reaction.

8. The method of claim 1, wherein the compound of formula (7) is prepared by the reaction of an aldehyde, oxalohydrazide and ammonia acetate: